Figure 1:
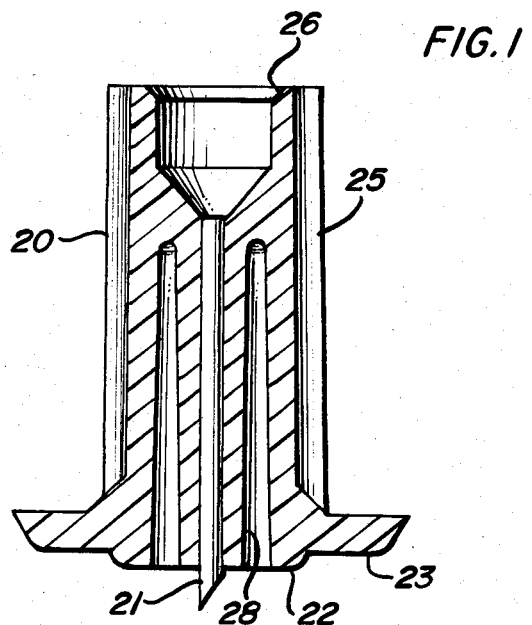
Figure 2:
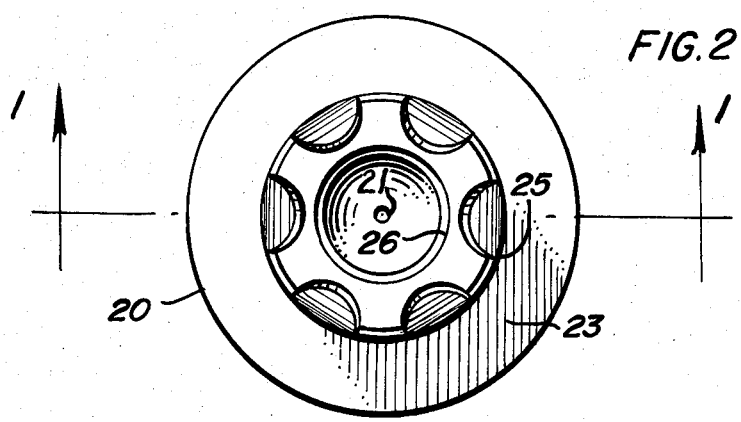
Figure 3:
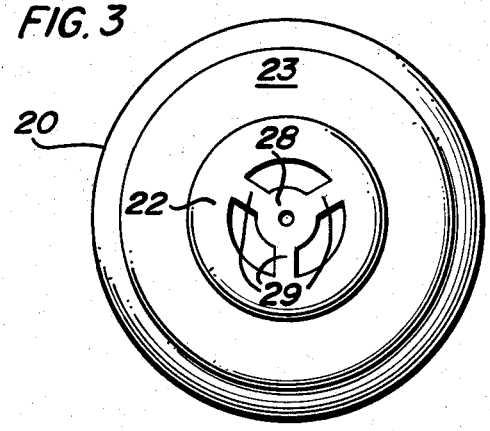

United States Patent [19]

Brennan et al.

[11] Patent Number: 4,607,632
[45] Date of Patent: Aug. 26, 1986

[54] SKIN TESTING DEVICE WITH FUNNEL LOADING

[75] Inventors: Cynthia B. Brennan; Louis G. Brennan, both of Stockton, Calif.

[73] Assignee: Aller-Screen, Inc., Stockton, Calif.

[21] Appl. No.: 605,249

[22] Filed: Apr. 30, 1984

[51] Int. Cl.⁴ ............................................. A61B 10/00
[52] U.S. Cl. ...................................... 128/743; 604/47
[58] Field of Search .................... 128/743; 604/47, 46, 604/117

[56] References Cited

U.S. PATENT DOCUMENTS

| | | | |
|---|---|---|---|
| 2,841,138 | 7/1958 | Laub | 128/743 |
| 3,221,740 | 12/1965 | Rosenthal | 604/47 |
| 3,596,660 | 8/1971 | Melone | 604/47 |
| 4,222,392 | 9/1980 | Brennan | 128/743 |

Primary Examiner—Edward M. Coven

[57] ABSTRACT

A skin test kit and novel injection unit for intracutaneous use. A hollow cannula scarifier is loaded with a fluent test substance through a funnel.

7 Claims, 5 Drawing Figures

SKIN TESTING DEVICE WITH FUNNEL LOADING

DESCRIPTION

This invention relates to skin testing with biological substances. In particular, it relates to diagnostic techniques and devices for allergy detection, including intracutaneous injection of biologicals, such as aeroallergens, food allergens, and other chemical substances. In particular it relates to an improved injection unit and test kit.

In the past diagnosis of allergies has depended upon introducing various biological substances to the epidermis or dermis. In a widely-accepted testing method for inhalant allergy—the scratch test—various allergenic substances are applied by abrading or cutting the epidermal layer and contacting a liquid allergenic extract or the like with the exposed skin tissue. These test areas are often on the back of a human patient, who may be subject to many painful tests. Recently an allergy testing system was devised for invivo intracutaneous use comprising a pointed cannula injection unit for carrying biological or chemical test substances. In U.S. Pat. Nos. 4,205,689, and 4,222,392 (incorporated herein by reference) novel applicator skin test devices and multiple allergen screening procedures are described. This device includes an applicator or injection unit having a hilt or flat plate portion and a hollow rigid handle portion attached to the plate portion on one side thereof and adapted for grasping the device. In order to pierce the skin, a hollow metal cannula scarifier element is mounted on the flat plate, extending outwardly from the flat plate opposite the handle portion a predeterminded length for intradermal injection. The cannula has a sharp skin-piercing point at its lower extremity and a shaft portion extending upwardly through the flat plate into the hollow handle portion. This configuration permits the device to be loaded with a predetermined amount of fluent skin testing substance, which may be applied to the point by dipping and distributed into the hollow scarifier by capillary action. This technique uses an allergy testing kit for multiple allergen screening and may be assembled with a number of applicators or injection units. A base member comprising one or none recessed depressions having a well portion adapted to receive a needle-like prong is provided with the kit. A corresponding number of intracutaneous injection units adapted for being held in the recessed depression of the base member is provided, each comprising a hilt portion adapted for insertion into a comlementary recessed depression of the base member. A downwardly extending skin test prong portion is adapted for insertion into the corresponding well. The upwardly extending handle portion can be grasped manually for applying the injection units sequentially. In a typical test kit at least one of the prongs is loaded with a mixture of biologically active allergens, and at least one of the prongs is loaded with a diluent devoid of biologically active substance for test control.

When a thin cannula, such as a standard 20 gauge hypodermic needle is employed as the hollow scarifier element, a relatively small amount of antigen-diluent mixture is required to reach the capillary capacity. For instance, if a drop of liquid test substance is placed in a well and filled by dipping, the capillary action may take up only about 2 milligrams or less. Thus, the amount of test substance injected during the skin test may be only a small fraction of the total amount lost in the loading procedure.

It has been found that loading efficiency may be increased by an improved injection unit structure and skin test kit assembly. Rather than fill a base well with a large quantity of test substance and load by capillary uptake, a novel loading technique employs a funnel structure adapted to receive a predetermined quantity of liquid test substance. The funnel is in fluid communication with the hollow cannula whereby at least a portion of the dispensed liquid is passed through the funnel to the hollow cannula.

Accordingly, it is an object of the present invention to provide a skin test device for intracutaneous use comprising: a flat plate portion; an open-topped rigid handle portion attached to the plate portion on one side thereof and adapted for manually grasping the device; a funnel disposed at the top of said handle poriton; and a hollow metal cannula scarifier element mounted inside said handle and extending outwardly from said flat plate opposite said handle portion for intracutaneous injection said scarifier having a sharp skin-piercing hollow point at its lower extremity and an upper shaft portion extending upwardly through said flat plate in fluid communication with said funnel fluid; whereby said device may be loaded with a predeterminded amount of fluent skin testing substance applied through said funnel and distributed into the hollow scarifier by capillary action. In a preferred embodiment the handle portion comprises an elongated outer member having an open top end, and an inner sleeve member projecting downwardly through the hollow handle portion for holding the shaft portion of the scarifier element firmly with the predetermined length exposed below said flat plate portion.

This applicator device can be used advantageously with base and lid members of a test kit to facilitate loading, particularly when the kit is preloaded prior to closure. It is a further object to provide a skin test for invivo intracutaneous use including a base member having base well means for holding liquid test substance and having at least one depression for receiving hand holding a corresponding injection unit in cooperation with lid means, the injection unit comprising a plate portion adapted to be received by the base well means for containing the liquid test substance. An open-top handle portion is attached, as by integral molding, to the plate portion on one side thereof and adapted for manually grasping the device, and a hollow cannula element is mounted on the plate extending outwardly from the plate opposite the handle portion a predetermined length for intracutaneous injection. The cannula has a sharp skin-piercing point at its lower extremity an upper shaft portion extending upwardly through the plate into the handle portion; whereby the device may be loaded with a predetermined amount of fluent skin testing substance applied to said point and distributed into the cannula by capillary action. The improvement herein comprises funnel means communicating with the cannula element for applying liquid test substance through said funnel means. Advantageously, the handle portion is formed with an integral interior funnel tip provided with a downwardly sloping interior surface terminating inwardly at an upper end of the hollow cannula, whereby liquid test substance dispensed into the top funnel-shaped handle portion is permitted to flow by gravity into the hollow cannula. The skin test kit further comprises kit lid means for fitting over the base member to enclose the injection unit and having a gas-tight slidable peripheral seal whereby closure of the kit lid means can force liquied form the funnel top into the base well means. These and other objects and features of the invention will be seen in the following description of preferred embodiments and in the drawings.

BRIEF DESCRIPTION OF THE DRAWINGS

FIG. 1 is a vertical cross-section view of an improved injection unit for allergen application according to the present invention;

FIG. 2 is a top view of the preferred injection unit;

FIG. 3 is a bottom view of the injection unit;

FIG. 4 is a typical allergy test kit, shown in vertical cross-section view, with an alternative injection unit; and FIG. 5 is a longitudinal cross-section view of another embodiment having integrally formed parts.

An enlarged sectional view of a single injection unit 20 in depicted in FIG. 1. In this preferred embodiment, a metal cannula is held firmly in the hilt portion of the injection unit. The hilt portion comprises a flat plate, with a two-tier configuration 22, 23. The handle portion 25, shown as an elongated member, may have a funnel opening at its top end to permit access to the injection unit. This aids in manufacture, liquid loading and sterilization of the fabricated applicator system. To provide a firm gripping force on the cannula 26, the flat plate or hilt portion 22 of the injection unit has an inner sleeve 28 extending through the handle portion. This prevents slippage during use of the cannula 21 as a scarifier, with a predetermined length exposed below the flat plate or hilt 22, 23. In order to prevent distortion of an integrally molded injection unit, inner sleeve member 28 is held spaced apart from the other handle shell portion 25 by a plurality of molded longitudinal ribs 29, as shown in FIG. 3. The annular cavity between the sleeve and handle shell helps prevent burnout during thermoplastic molding and provides dimensional stability to the device.

The preferred injection unit of FIGS. 1–3 is made of molded cyclolac ABS plastic. The handle is hollow and the elongated tubular shape permits easy grasping. The cannula point and shaft pierce the center of the two-tier circular hilt, which is molded with a diameter slightly less than the cannula to provide means for holding the cannular in a fixed position by radial gripping force.

The applicator prong or skin-piercing poriton of the 1njection unit may be made from several materials, preferably metal and hard plastics. Polished surgical steel cannulae are the prong members found to be advantageous from the standpoint of quality and reproducibility. The standard hypodermic needle or cannula of polished steel, having a bevel angle of 12.5°, provides a sharp point which can easily be inserted to the desired skin depth. A standard cannula of 15 to 25 gauge can be employed, depending upon the desired carrying capacity of the base structure and prong size. For a wide variety of biological substances, a standard 20 gauge cannula can provide the dual functions of the prong member. The diluent of fluid carrier of the biologicals is often a hydrophilic compound or mixture of chemicals which possesses a high surface tension with respect to the prong. A capillary-forming structure permits relatively large amounts of the liquid biological substances and carriers to adhere to the prong. Typically, a 20 gauge steel needle has been found to retain about 1.8 milligrams of antigen-diluent mixture.

While the amount of fluid varies according to the particluar test compostion and prong type, amounts from a few tenths of a milliliter to a few microliters may be feasible. For allergenic extracts of the kinds described herein, a loading of about 0.001 to 0.1 ml is preferred. Liquid pickup from the funnel structure would ordinarily be in the desired range if a fractional milliliter of liquid extract or chemical mixture is dispensed. It is understood that a controlled amount of solid or semi-dried biological can be obtained by employing more or less diluent to adjust the active component of the mixture. A relatively large amount of antigen can be picked up by surface phenomena when less diluent is present. For purposes of product uniformity, the amounts of antigen components may be established for manufacturing convenience or medical purpose.

Plastic molding compositions, such as ABS, (acrylonitrile, butadiene, styrene copolymer) nylons, polyalkenes, polycarbonates, acrylics, etc. can be employed in making the injection units, bases, covers, etc.

The flat base of the applicator may be two-tiered with a central smaller portion adjacent to the cannula and a larger portion near the handle. This type of base disguises the needle puncture and serves as a stop to control depth of the penetration of the point of the test prong. This feature makes the needle puncture virtually painless and insures repetitive, standardized penetration of the skin to the desired depth. An alternative design is a completely flat or concave hilt. Aside from the obvious advantage of the hypodermic needle point, i.e., sharp relatively atraumatic skin puncture, there are other advantages. These advantages are the utilization of the inner bore of the needle, in the area of the cutting point or bevel, as an inherent capillary trough or liquid reservoir for antigen application.

The needle point may project from the circular base anywhere from 0.5 to 3.0 mm or more, with 2.25 mm being optimum for most applicators. The injection unit permits the length of needle point projection to be varied without changing the cavity mold used in manufacture. During loading of liquid biologicals or other fluid materials, the cannula may be received into a well to prevent damaging the point as shown in FIG. 4.

During use for skin testing, the injection unit 20 is removed manually from the base and inserted into the skin. The hollow metal scarifier element 21 pierces the epidermal layer and extends there through into the dermis, where the substance carried on the scarifier prong is deposited intracutaneously. Ordinarily, the injection unit is withdrawn immediately after injecting the test substance.

The base member 110 may be packaged as part of a testing kit, as shown in FIG. 4. The base is provided with a plurality of circular depressions 112 into which the hilt portion of alternative injection unit 120 is inserted. The bottom of this recessed portion may be tapered downwardly to a depth of about 3 mm, permitting the lower prong tip to be accommodated within a well 114, which may be conoidal in shape. After inserting the injection unit, a measured quantity of the particular biological substance or diluent is place in the funnel means. In order to protect the testing kit after manufacture and sterilization, a lid 118 is placed over the base member 110, preventing the individual injection units from becoming loose. As an extra precaution, a projecting segment 116 can be molded onto the base 110 to engage or retain the hilt portion in its nested position, thus preventing dislocation of the applicator parts during shipment. The lid may be peripherally taper-fitted with the sides of base member 110 to prevent contamination of the applicator and/or antigens. The lid and base may be spot-fused to prevent disassembly prior to use. The encloure formed by the base and lid may be presterilized or, advantageously, made or of material permeable to a sterilant gas. For instance, various polyalkenes, such as polyethylene, may be employed as the package material when using ethylene oxide/freon gas for post-assemble sterilization. Alternatively, the entire testing kit may be inserted in an envelope having a gas-permeable window.

Figure 4:
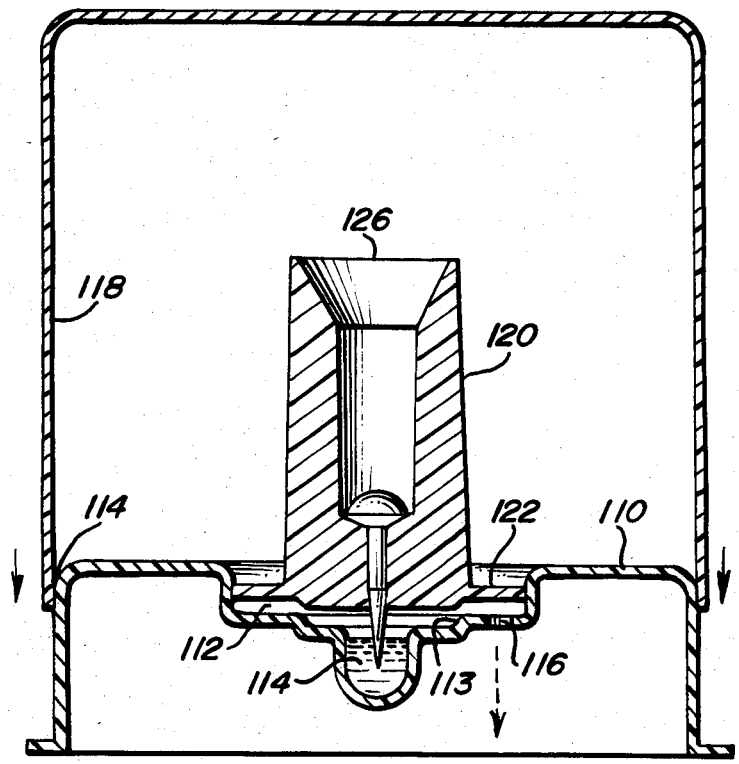

In the preferred loading procedure, a measured quantity, usually a fraction of a milliliter, is applied dropwise or by micropipetting into the top portion 126 of the injection unit 120. The funnel structure is provided with downwardly sloping interior surface 127 which terminates at the upper end of the hollow cannula, into which the liquid test substance passes by gravity and capillary flow. Since the amount of dispensed liquid exceeds the capillary capacity of the cannula, a portion of the liquid can be accumulated at the lower end of the injection unit, as shown in FIG. 4. A positive pressure may be applied to the liquid in funnel means 127 to drive the liquid into the bottom well. This is achieved following assembly of the injection unit(s) into the kit base 110 by fitting a lid 118 having a gas-tight slidable seal 119 over the periphery of the base. Closure of the lid onto the base creates a gas pressure, forcing liquid from the top funnel portion through the cannula into the base well means, where the liquid is stored in contact with the cannula tip.

The preferred embodiment of the test kit depicted in FIG. 4 shows a vertical cross section of a molded receptacle 110 adapted to receive an applicator 120. The circular applicator disc portion 122 for this configuration is closely mated to the periphery of the base well, thereby resiliently holding the applicator or injection unit with sufficient firmness to prevent separation during handling.

The base portion shown comprises a concentric depression 112, annular ridge 113 and central well 114. A measured quantity of liquid antigen is placed into the funnel after the injection unit is inserted into the depression with the cannula point extending into the well. A small vent hole 116 located between the annular ridge 113 and the periphery of the depression 112 permits air or other gas to be evacuated. By venting the trapped gas, no excessive pressure is permitted to build in the well 114. The hilt portion 122 of the applicator is seated against the annular ridge 113, forming an effective liquid seal.

This configuration retains a normal capillary loading of the desired amount of antigen at the lower extremity of the cannula. Antigen amounts beyond the normal capillary filling might result in lack of standardization for the intracutaneous deposit. In the emobodiment of FIG. 4, the base may be molded of impact polystyrene advantageously, and the lid may be of the same or different material. ABS type resin ("cycolac") is preferred for the injection unit.

While the preferred testing method employing the new applicators involves a manual sequence in which the individual injections are spaced at least about 2 cm apart on the skin: it is understood that the invention may be adapted or modified to permit simultaneous pickup and application of the entire multi-unit assembly. This can be accomplished by a suitable manipulator device adapted to receive and hold the handle portion of the individual injection units in spaced relationship. However, difficulties in avoiding blood vessels must be taken into account for any such multipoint application.

Figure 5:
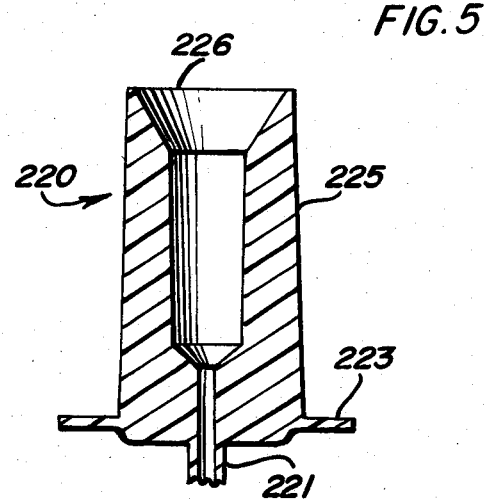

An alternative applicator embodiment is shown in FIG. 5, wherein a skin test device 220 is depicted in vertical cross-section view. This embodiment provides an integrally molded structure, including a hollow open-topped handle portion 225, having a funnel 226, plate portion 223 and a hollow scarifier 221 has a star-shaped array of multiple abrading elements for application of test liquid to skin. This device may be molded thermoplastic, metal, etc., and the scarifier element may also have a serrated abrading surface. This modification can be loaded as previously described, with test liquid being applied to the skin by twisting or rocking the applicator device to scratch the skin.

I claim:

1. A skin test kit for invivo intracutaneous use including a base member having base well means for receiving a cannula point and holding liquid test substance, said base member having at least one depression for receiving and holding a corresponding injection unit in cooperation with kit lid means, said injection unit comprising a plate portion received by said base member; an open-top handle portion attached to the plate portion on one side thereof; a hollow cannula element mounted on said plate and extending outwardly from said plate opposite said handle portion a pre-determined length for intracutaneous injection, said cannula having a sharp skin-piercing point at its lower extremity; said handle portion having an integral interior funnel top provided with a downwardly sloping interior surface terminating inwardly at an upper end of said hollow cannula and communicating with said cannula element for applying liquid test substance through said funnel means; and said kit lid means fitting over said base member to enclose said injection unit and having a gas-tight slidable peripheral seal whereby closure of said kit lid means can force liquid from the funnel top into the base well means.

2. The skin test kit of claim 1 wherein said handle portion, cannula element and plate portion are integrally formed and provided with multiple abrading elements.

3. A skin test device for intracutaneous use comprising:
   a flat plate portion;
   an open-topped rigid handle portion attached to the plate portion on one side thereof;
   a funnel disposed at the top of said handle portion;
   a hollow metal cannula scarifier mounted inside said handle portion and extending outwardly from said flat plate portion opposite said handle portion for intracutaneous injection, said scarifier having a sharp skinpiercing hollow point at its extremity and an upper shaft portion extending upwardly through said flat plate portion in fluid communication with said funnel, whereby said device may be loaded with a predetermined amount of fluent skin testing substance applied through said funnel and distributed into the hollow scarifier; said handle portion comprising an elongated outer member having an open top end, and an inner sleeve member connected to said outer member proximate the open top end projecting downwardly through said hollow handle portion for holding the shaft portion of the cannula scarifier firmly with the predetermined length exposed below said flat plate portion.

4. The test device of claim 3 wherein the cannula has a controlled capillary liquid loading capacity of about 0.001 ml to about 0.1 ml and an exposed length of about 0.5 to 3 mm.

5. The test device of claim 3 wherein the inner sleeve member is held spaced apart from the outer handle member by a plurality of longitudinal ribs.

6. An injection unit for intracutaneous allergenic skin test use comprising:

a molded open top plastic body having a hilt portion, an upwardly extending handle portion attached to said hilt portion on one side thereof, and top-loading funnel means for receiving allergenic liquid; downwardly extending skin test prong means connected in fluid communication with said funnel means for loading of liquid from the funnel means and including prong reservoir means for receiving and holding a predetermined amount of liquid for intracutaneous deposition and a sharp skin-piercing prong point extending about 0.5 to 3 mm. from said hilt.

7. A skin test kit including at least one injection unit according to claim 6, and further comprising a base member having base well means for receiving said test prong and for containing allergenic liquid; lid means for fitting over said base member to enclose said injection unit and having a gas-tight slidable peripheral seal whereby closure of said lid means can force liquid from the funnel into the base well means; and said base member having at least one depression for receiving and holding said injection unit in cooperation with said lid means.

* * * * *